United States Patent
Lombardi

(10) Patent No.: US 7,449,547 B2
(45) Date of Patent: Nov. 11, 2008

(54) PROCESS FOR THE SYNTHESIS OF DISTAMYCIN AND DERIVATIVES THEREOF USING 1-METHYL-4-FORMYLAMINO-2-PYRROLE CARBONYL CHLORIDE ITERATIVELY AS AN INTERMEDIATE

(75) Inventor: Paolo Lombardi, Cesate (IT)

(73) Assignee: Naxopharma S.r.l., Cesate (IT)

( * ) Notice: Subject to any disclaimer, the term of this patent is extended or adjusted under 35 U.S.C. 154(b) by 185 days.

(21) Appl. No.: 10/557,424

(22) PCT Filed: May 28, 2004

(86) PCT No.: PCT/EP2004/005821

§ 371 (c)(1),
(2), (4) Date: Nov. 18, 2005

(87) PCT Pub. No.: WO2004/106301

PCT Pub. Date: Dec. 9, 2004

(65) Prior Publication Data

US 2007/0060523 A1    Mar. 15, 2007

(30) Foreign Application Priority Data

Jun. 3, 2003    (IT)    ................... MI2003A1111

(51) Int. Cl.
*C07D 207/34*    (2006.01)
(52) U.S. Cl. .................. 530/338; 548/530; 548/532
(58) Field of Classification Search .................. None
See application file for complete search history.

(56) References Cited

U.S. PATENT DOCUMENTS 5,670,534 A * 9/1997 Animati et al. ............. 514/422

OTHER PUBLICATIONS

Bialer et al: "A Total Synthesis of Distamycin A, an Antiviral Antibiotic" Tetrahedron, vol. 34, 1978, pp. 2389-2391, XP002293994 cited in the application scheme, p. 2390.
Grehn et al: "Novel Efficient Totel Synthesis of Antiviral Antibiotic Distamycin A" Journal of Organic Chemistry vol. 46, 1981 pp. 3492-3497 XP002293995 scheme I p. 3494.

* cited by examiner

*Primary Examiner*—Jeffrey Edwin Russel
(74) *Attorney, Agent, or Firm*—Modiano & Associati; Albert Josif; Daniel J. O'Byrne

(57) ABSTRACT

A process for the total synthesis of Distamycin, and synthetic poly-(4 aminopyrrole-2-carboxamide) congeners thereof, using 1-methyl-4-forinylamino-2-pyrrolecarbonyl chloride iteratively as an intermediate, is provided. The process finds application for both in solution and solid support synthetic technologies.

5 Claims, No Drawings

PROCESS FOR THE SYNTHESIS OF DISTAMYCIN AND DERIVATIVES THEREOF USING 1-METHYL-4-FORMYLAMINO-2-PYRROLE CARBONYL CHLORIDE ITERATIVELY AS AN INTERMEDIATE

FIELD OF THE INVENTION

The present invention relates to a process for the manufacture of poly-(4-aminopyrrole-2-carboxamide) compounds of general formula (I):

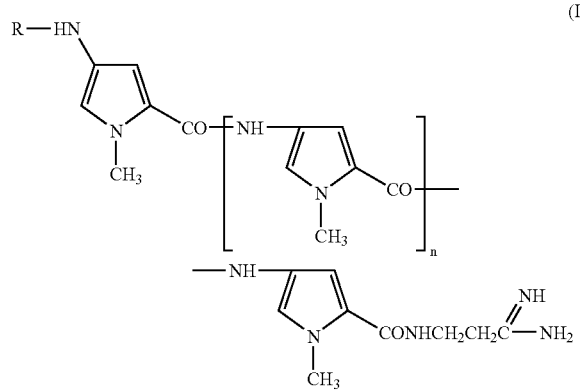

wherein: R is CHO or H; n is 0 or an integer comprised between 1 and 10 and, more specifically, (I) is (Ia) when R is CHO, and (I) is (Ib) when R is H, starting from and using the intermediate 1-methyl-4-formylamino-2-pyrrolecarbonyl chloride of formula (II):

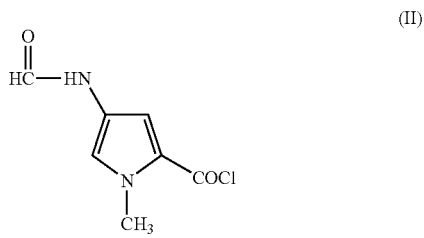

according to an iterative process entailing repeated acylation and deformylation steps, respectively.

When n is 1, the compound of formula (Ia) is the well known antiviral antibiotic Distamycin which, according to the literature, is capable to interact reversibly and selectively with (dA-dT)-rich sequences in the DNA minor groove, thus interfering with both replication of genetic message and transcription processes [K. R. Fox & H. J. Waring, Nucleic Acids Res. 12:9271 (1984); R. S. Youngquist & P. B. Dervan, Proc. Natl. Acad. Sci. USA, 82:2565 (1985); S. Neidle et al., Biochem. J. 243:1 (1987)]. Distamycin has been isolated from and produced by the mycelium of *Streptomyces distallicus* [A. M. Casazza et al., Antimicrobial Agents Chemother, 5:593 (1965)] and selectively inhibits the multiplication of different viruses including Vaccinia, Herpes simplex, Rous sarcoma virus and, additionally, the multiplication of *Plasmodium falciparum*, the causative agent of malaria [M. Verini et al., Il Farmaco 10:705 (1976); N. Mongelli et al., GB 2235381A]. Moreover, it has been demonstrated that higher analogues of Distamycin of formula (Ia), wherein n is 2, 3, and 4, exhibit a marked improvement in the above mentioned pharmacological properties [F. Arcamone et al., Gazz. Chim. Ital., 99:620 (1969)].

The compounds of formula (Ib), on their turn, have been linked with alkylating groups, e.g., nitrogen mustards, on the N-terminus moiety to furnish products which have been reported as potential anticancer agents [F. Arcamone, et al., J. Med. Chem., 32:774 (1989); P. Cozzi, et al., Curr. Pharm. Design, 4:181 (1998)].

Moreover, the compounds of formula (Ib) have been also linked with the 1-methyl-4-carbamoyl-2-pyrrolecarbonyl group on the N-terminus moiety to furnish products described having improved antiviral and antimalarial properties and better therapeutic index with respect to Distamycin [A. Alfieri et al., Antiviral Chem. Chemother., 8:243 (1997); P. Lombardi et al., Pharmacol. Ther., 76: 125 (1997); WO 94/25436].

BACKGROUND OF THE INVENTION

As noted herein before, Distamycin is produced from the fermentation of the mycelium of *Streptomyces distallicus*, and higher analogues bearing a greater number of pyrrole units are described to be prepared by semisynthesis starting from Distamycin itself obtained from the fermentation, following cumbersome chemical processes. It is clear that such a biotechnological process requires specialized equipments, apparatuses, and personnel which not always are easily available in a standard chemical industry, usually equipped with general use chemical reactors. Moreover, the producing microrganism strain and production technology have not been disclosed and the art is still a corporate know-how of the company which discovered Distamycin.

Accordingly, a number of total syntheses of Distamycin have been accomplished. Apart from small variations, the majority of the syntheses disclosed in the art utilize the key intermediate 1-methyl-4-nitro-2-pyrrolecarboxylic acid of formula (III):

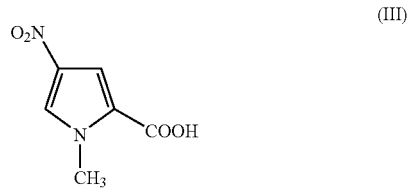

(or its chemical equivalent 1-methyl-4-nitro-2-trichloacetylpyrrole) to obtain nitropyrrolecarboxyamide or aminopyrrolecarboxyamide intermediates of general formula (IV):

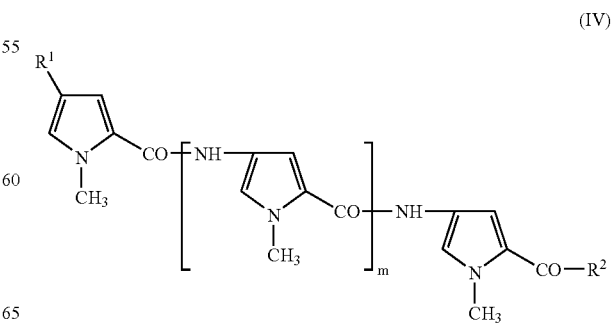

wherein: $R^1$ is $NO_2$ or $NH_2$, $R^2$ is alcoxy or $NH—CH_2CH_2CN$, and m is 1 or 2, by repeatedly alternating the catalytic hydrogenation step of the 4-nitro group with the acylation step of the resulting amino group with a suitable acylating derivative of the compound of formula (III), [F. Arcamone, et al., Gazz. Chim. Ital. 97:1110 (1967); M. Bialer, et al., Tetrahedron 34:2389 (1978); J. W. Lown, et al., J. Org. Chem. 50:3774 (1985); M. Shibuya, et al., Heterocycles, 27:1945 (1988)].

It is evident that the above processes require three catalytic hydrogenation steps of the nitro group, i.e. as many as the number of pyrrole rings of Distamycin. It is also evident that the number of the above mentioned hydrogenation steps will inevitably increase following increasing in the number of methylpyrrole rings, when there is provided the preparation of higher homologues of Distamycin of formula (Ia, n≧2) which, as noted herein before, show improved and more interesting bioactivities, affecting the economy and viability of the synthetic process.

Moreover, the above mentioned syntheses imply the introduction of the formyl group onto the amino group of the N-terminus moiety of the compounds of formula (Ib) at the completion of the assemblage of the required pyrrole rings. It is known in the literature and in the art that the N-formylation reaction of amidine-compounds of formula (Ib) is a troublesome, or at least unsatisfactory, process to accomplish, above all in the case of the preparation of higher analogues of Distamycin bearing a greater number of pyrrole units.

Synthetic alternatives directed to reduce the number of catalytic hydrogenation steps of the nitro group, and to avoid the introduction of the formyl group onto the amino group of the N-terminus moiety at the completion of the assemblage of the required pyrrole rings, extensively utilized both uncommon reagents and protective groups, such as those typically used for coupling reactions in the peptide chemistry, as well as column chromatography for the purification of a number of intermediates thereon, rendering the overall synthetic process poorly viable and scalable [Grehn, L., et al., J. Org. Chem. 46:3492 (1981)].

Moreover, all the above mentioned syntheses entail the transformation reaction of the C-terminus nitrile group in the C-terminus amidine group sinner reaction) at the completion of the assemblage of the required pyrrole rings.

Therefore, it is evident that there are no state-of-the-art synthetic alternatives, from the point of view of process viability, economy and scalability, to the biotechnological production of Distamycin and, more generally, to the production of poly-(4-aminopyrrole-2-carboxamide) compounds of general formula (I).

The present inventor intends to get round the disadvantages inherent to the above mentioned total syntheses of distamycin and, in general, of poly-(4-aminopyrrole-2-carboxamide) compounds of general formula (I), by using repeatedly and subsequently the intermediate 1-methyl-4-formylamino-2-pyrrolecarbonyl chloride of formula (II) in iterative alternating acylation—deformylation steps to assembly the polypyrrolecarboxamide backbone.

The compound of formula (II), so far not yet disclosed, turned to be surprisingly stable and, in the same time, chemically reactive to allow the polymerisation of the same under suitably controlled conditions to obtain the assemblage of the polypyrrolecarboxamide backbone of the desired length, avoiding the number of catalytic hydrogenation steps of the nitro group and the unsatisfactory introduction of the formyl group at the end of the pyrrolecaboxamide backbone assemblage in the case of the preparation of compounds of formula (Ia).

Therefore, the present invention provides a total synthetic process to make distamycin and, more generally, the poly-(4-aminopyrrole-2-carboxamide) compounds of general formula (I), which is more economical and alternative with respect to both the biotechnological production of distamycin (including analogues and intermediates thereof obtained by semisynthesis from fermented distamycin) and the total syntheses of the compounds of formula (I) known in the art.

According to a first aspect of the present invention, the formyl group which serves as a protecting group of the amine group at the N-terminus during the course of the synthetic process, will be present, if desired, as the functional group characterizing the final product of general formula (Ia).

A further aspect of the present invention is, therefore, a process for the manufacture of the compounds of formula (Ia), as above described; which process does not entail the formylation of the amine group at the N-terminus moiety of the corresponding compounds of formula (Ib).

A further aspect of the present invention is, therefore, a process for the manufacture of the compounds of formula (Ib), as above described, by deformylating the corresponding compounds of formula (Ia), as above described.

DETAILED DESCRIPTION OF THE INVENTION

The present invention provides an iterative process for the manufacture of poly-(4-aminopyrrole-2-carboxamide) compounds of general formula (I), as above described.

The provided process makes use of the 1-methyl-4-formylamino-2-pyrrolecarbonyl chloride of formula (II) as a key intermediate, which is used both as a starting material and repeatedly as synthetic building block intermediate for the assemblage of the compounds of general formula (I).

Therefore, according to an embodiment of the present invention (Scheme 1) the acyl chloride of formula (II) may be prepared starting from the 1-methyl-4-formylamino-2-pyrrolecarboxylic acid of formula (V) following conventional procedures for the formation of acyl chlorides well known to the expert in the art, for instance by using thionyl chloride; sulphuryl chloride, oxalyl chloride, etc., in a suitable solvent such as benzene, toluene, chlorinated solvents or ethers, at a reaction temperature ranging from 0° C. to 100° C. Thionyl chloride in benzene at about 50° C. is preferred.

SCHEME 1

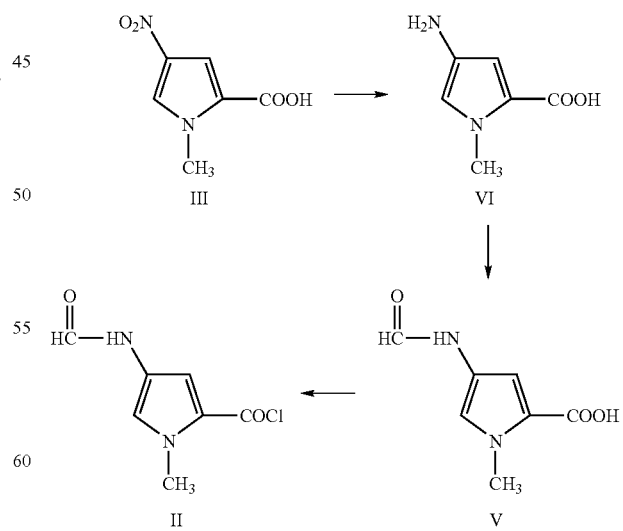

By simple and repeated removal of the reaction solvent in vacuo, the product of formula (II) is surprisingly isolated as a solid which unexpectedly proved also stable and suitable for long term storage, notwithstanding the product (II) is represented by a small crowded molecule bearing two chemically reactive groups.

The N-formylaminopyrrolecarboxylic acid of formula (V), on its turn, may be obtained by formylation of the 4-aminopyrrolecarboxylic acid (VI) following known methods, for example by using acetoformic anhydride (Grehn, L., et al., J. Org. Chem. 46:3492 (1981)), for example, and preferably, the reaction may be carried out with N-formylimidazole (WO 92/09574 A2).

The 1-methyl-4-aminopyrrolecarboxylic acid (VI) may be prepared from the 1-methyl-4-nitro-2-pyrrolecarboxylic acid of formula (III) by reducing the nitro group, e.g., by catalytic reduction according to known and established methods referred in the above cited literature. This is the only reduction step of the nitro group required by the synthetic process of the present invention.

According to another embodiment of the present invention (Scheme 2), the 1-methyl-4-formylamino-2-pyrrolecarbonyl chloride of formula (II), obtained as above described, is reacted with 3-aminopropionitrile, following known methods for amine acylation, e.g., in presence of inorganic or organic bases such as sodium carbonate, sodium bicarbonate, sodium hydroxide or diethylamine, triethylamine, diisopropylethylamine in suitable solvents such as alkanols, ethers, water, preferably with diisopropylethylamine in tetrahydrofuran, and then directly subjected to the known Pinner reaction (A. Pinner et al., Chem. Ber. 10:1889 (1877)) with the purpose to introduce the propionamidine group, functional feature of the C-terminus moiety of distamycin and its oligo- and poly-pyrrolecarboxamide congeners of general formula (I). Under the conditions of the Pinner reaction, surprisingly the formyl group is cleaved to give the 4-aminopyrroleamidine compound of formula (VII) directly. The compound (VII), thus obtained, is acylated at the 4-amine group with 1-methyl-4-formylamino-2-pyrrolecarbonyl chloride of formula (I), e.g., according to the above mentioned methods, preferably in the presence of diisopropylethylamine in tetrahydrofuran/methanol to yield the oligopyrroleamidine compound of formula (Ia, n=0).

The N-formylpyrroleamidine dimer (Ia, n=0), thus obtained, if desired, is subjected, (A), to acidic hydrolysis, e.g., with hydrochloric, hydrobromic, p-toluenesulphonic, methanesulphonic acid or with an acidic polymeric resin, etc, in suitable solvents, preferably protic solvents such as water or alkanols and mixtures thereof, preferably in methanol with the addition of hydrochloric acid. In such conditions, the formyl group is cleaved to give the oligopyrroleamidine compound of formula (Ib, n=0), exposing therefore the N-terminus amine group which, if desired, may be, (B), acylated with 1-methyl-4-formylamino-2-pyrrolecarbonyl chloride of formula (II), in the same conditions as indicated above, to yield Distamycin of formula (Ia, n=1).

SCHEME 2

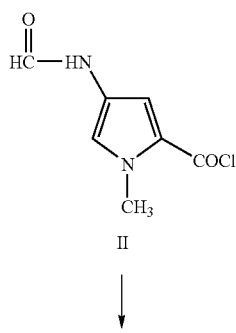

II

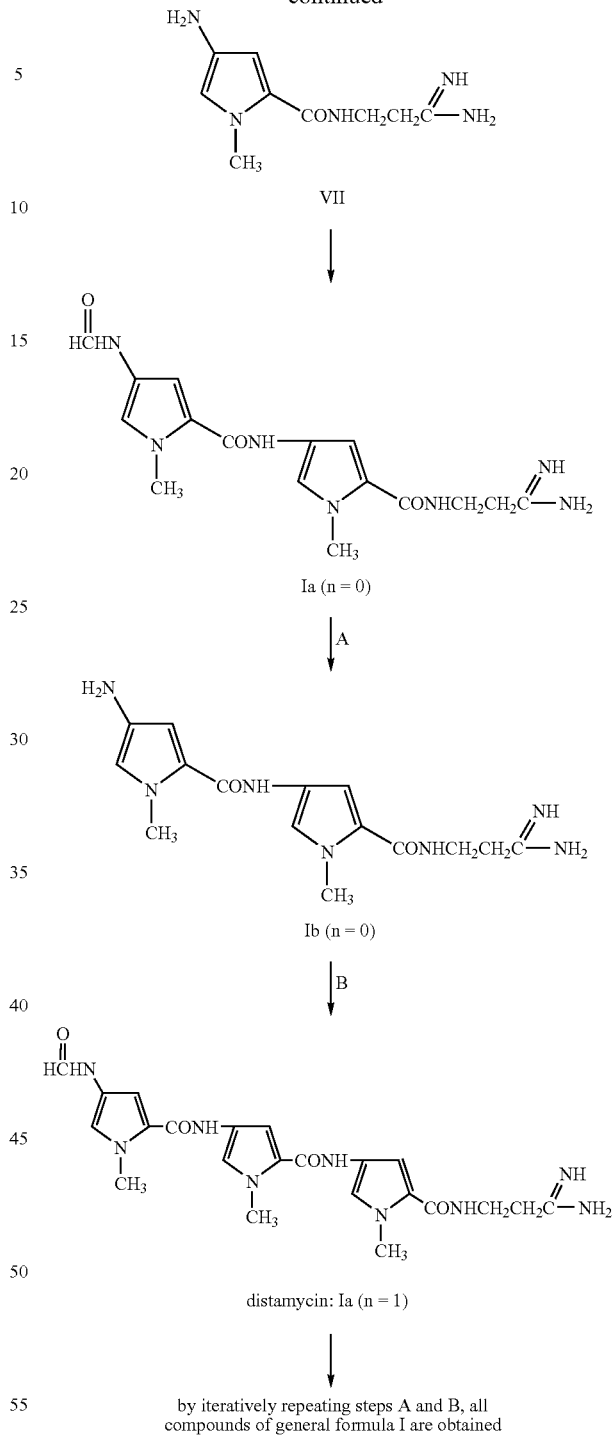

by iteratively repeating steps A and B, all compounds of general formula I are obtained If desired, the above described steps (A) and (B) may be repeated in an iterative fashion to give poly-4-(1-methylpyrrole)-2-carboxamide compounds of general formula (I).

An aspect of the present invention is, therefore, a process for the preparation of compounds of general formula (I), as previously described, where only a single reduction reaction of the nitro group is carried out.

Another aspect of the present invention is a process for the preparation of compounds of general formula (I), as previously described, where the amidine group is present since the beginning of the synthetic process.

A further aspect of the present invention is a process for the preparation of compounds of general formula (Ia), as previously described, where the N-formyl group is present since the beginning of the synthetic process.

Yet, a further aspect of the present invention is a process for the preparation of compounds of general formula (Ib), as previously described, which are obtained by deformylating the corresponding compounds of general formula (Ia).

Accordingly, an outstanding aspect of the present invention is a unique process for the manufacture of compounds of general formula (I), wherein n is an integer as previously indicated, starting from the corresponding (n−1) compounds described by the same general formula (I).

An applicative use of the present invention is the possibility to utilize the intermediate 1-methyl-4-formylamino-2-pyrrolecarbonyl chloride of formula (II) in place of the 1-methyl-4-nitro-2-pyrrolecarboxylic acid of formula (III) (or its chemical equivalent 1-methyl-4-nitro-2-trichloacetylpyrrole) in any of the above mentioned processes of the prior art, resulting in remarkable improvements to the same processes of the previous art, comprising the elimination of the many subsequent catalytic hydrogenation steps and of the N-formylation step at the accomplishment of the assemblage of the required pyrrole rings.

A further outstanding applicative use of the present invention (see Scheme 3) is the possibility to utilize the intermediate 1-methyl-4-formylamino-2-pyrrolecarbonyl chloride of formula (II) for the solid phase preparation of numerous poly-(4-(1-methylpyrrole)-2-carboxamide) compounds, analogues to the compounds of general formula (I) and endowed with relevant pharmacological activities (R. W. Burli & P. B. Dervan, Curr. Opin. Chem. Biol., 1999). There are provided in the art preparations of polymethylpyrrolecarboxamide compounds analogues to the compounds of general formula (I), comprising the growing of the pyrrole molecular backbone on a solid support (resin), onto which a suitable derivative of the 1-methyl-4-amino-2-pyrrolecarboxy monomer is initially linked, by subsequent iterative coupling with the same derivative (E. E. Baird & P. Dervan, J. Am. Chem. Soc., 118:6141 (1996); E. Vazquez et al., Tetr. Lett., 40:3621 (1999); N. R. Wurtz et al., Organic Lett., 3:1201 (2001)). Such preparations, even if implemented with the advantages which are inherent to the solid phase, such as, for example, ready isolation of synthetic intermediates, do not avoid the extensive use of expensive and poorly environment-friendly protecting groups, activating groups, coupling reagents, and cleaving reagents which are typical of the peptide chemistry, such as 9-fluorenylmethoxycarbonyl (Fmoc), t-butyloxycarbonyl (Boc), 2-(1H-tetramethyluronium hexafluorophosphate, hydroxybenzotriazole, 4-methylbenzhydrylamine, trifluoroacetic acid, ethandithiol, N,N-dimethylaminopyridine.

It has been surprisingly found that by applying the 1-methyl-4-formylamino-2-pyrrolecarbonyl chloride of formula (II) and the iterative synthetic steps (A) and (B) to the solid phase technologies above described, the use of the above mentioned protecting and activating groups and reagents is unnecessary, thus achieving further easiness and economy in the solid phase technology for the manufacture of the compounds disclosed by the above mentioned authors.

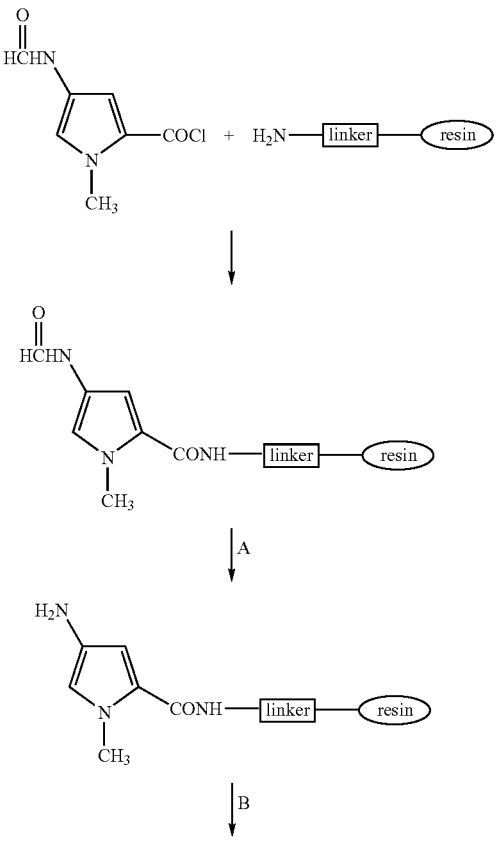

SCHEME 3

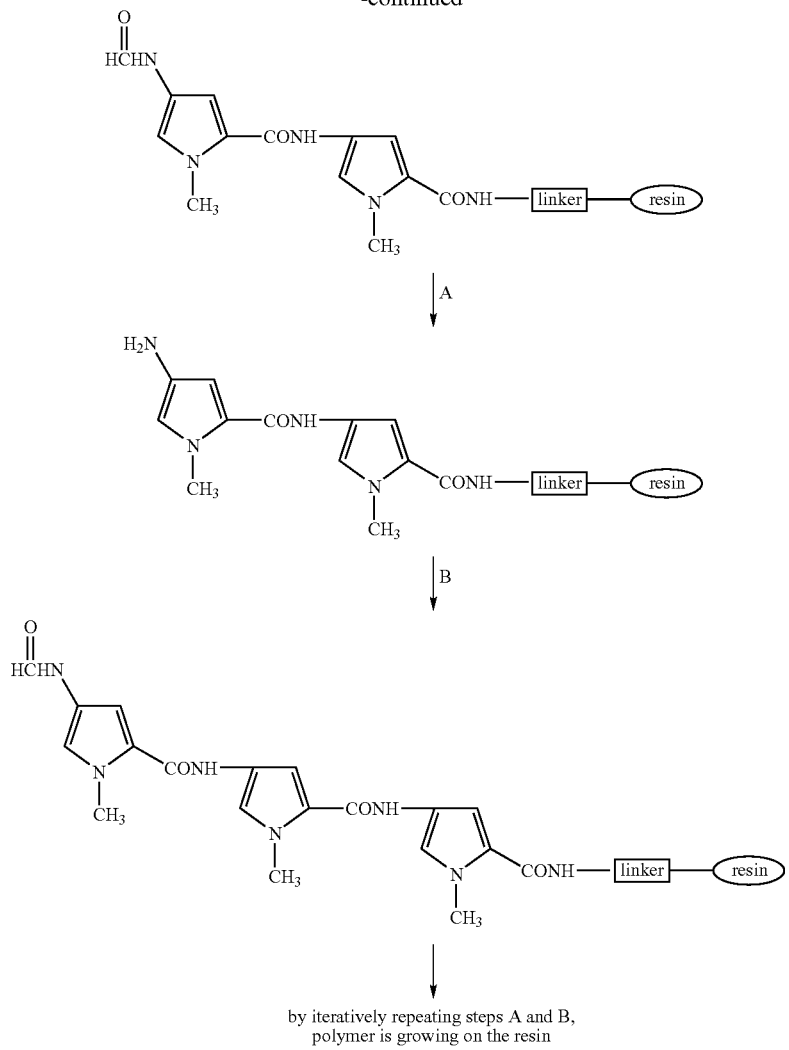

by iteratively repeating steps A and B,
polymer is growing on the resin

The following Examples are only intended to illustrate the invention without limiting the same.

EXAMPLE 1

1-methyl-4-formylamino-2-pyrrolecarboxylic acid (V).

1-methyl-4-nitro-2-pyrrolecarboxylic acid (III) (1.0 g, 6.0 mmol) is dissolved in 20 mL of a 1 M sodium carbonate aqueous solution and hydrogenated in presence of 250 mg of 10% Pd/C catalyst. When the uptake of hydrogen has stopped, the catalyst is removed by filtration and the resulting yellow solution, containing the aminoacid (VI), is slowly added to a freshly prepared benzene solution of N-formylimidazole with vigorous stirring. After the addition, the resulting two layers are stirred for additional 15 min and then the organic layer is separated and discarded. The aqueous yellow solution, cooled to 0-5° C., is carefully acidified with formic acid (pH 3.5) with vigorous stirring. The precipitated acid (V) is filtered off and washed with small portions of ice-cold water. There are obtained 0.81 g (yield 80%) of product (V): m.p. 208-210° C.; NMR (DMSO-d6), ppm: 3.85 (s, 3H); 6.75 (d, 1H); 7.35 (d, 1H); 8.15 (s, 1H).

EXAMPLE 2

1-methyl-4-formylamino-2-pyrrolecarbonyl chloride (II).

A suspension of 1-methyl-4-formylamino-2-pyrrolecarboxylic acid (V) in benzene is heated at 80° C. in presence of an excess of thionyl chloride until a solution is obtained. The reaction is then stopped. By repeatedly evaporating from benzene at reduced pressure and temperature, there is obtained the crude chloride (II) which is stocked and used without further purification following determination of the title (generally not below 60%) by conversion to an ester and quantitative analysis of the resulting ester derivative. IR: 1740 cm$^{-1}$.

EXAMPLE 3

3-(1-methyl-4-amino-2-pyrrolecarboxamido)propionamidine (VII).

To 1-methyl-4-formylamino-2-pyrrolecarbonyl chloride (II) (4.0 mmol) dissolved in 20 mL of tetrahydrofuran are added diisopropylethylamine (4.5 mmol) and 3-aminopropionitrile (4.5 mmol) with continuous stirring for 1 hour. The reaction mixture is evaporated under vacuum and the resulting crude product is washed with water several times and dried to be directly subjected to the above mentioned Pinner-reaction. To this are then added 25 mL of absolute ethanol and the resulting mixture, stirred and cooled with a dry ice—acetone bath, is saturated with gaseous hydrogen chloride. The reaction mixture is warmed to room temperature and stirred for additional 2 hours. Then, the solvent is removed under vacuum, the residue is taken up with absolute ethanol, cooled with a dry ice—acetone bath and saturated with anhydrous gaseous ammonia under vigorous stirring. The reaction mixture is warmed to room temperature and stirred for additional 1 hour. By evaporating the solvents under vacuum, the hydrochloride of the aminopyrrolepropionamidine compound (VII) is obtained as a white solid [60% yield based on chloride (II)]. NMR (DMSO-d6), ppm: 2.65 (t, 2H), 3.50 (t, 2H), 3.85 (s, 3H), 6.95 (d, 1H), 7.10 (d, 1H), 8.45 (t, 1H), 8.75-9.15 (br d, 4H), 10.2 (br s, 3H).

EXAMPLE 4

3-(1-methyl-4-(1-methyl-4-formylaminopyrrole-2-aminocarbonyl)pyrrole-2-carboxamido)propionamidine (Ia, n=0)

To a solution of 3-(1-methyl-4-amino-2-pyrrolecarboxamido)propionamidine (VII) hydrochloride, obtained from Example 3, in 15 mL of methanol is added a solution of an equimolar amount of crude 1-methyl-4-formylamino-2-pyrrolecarbonyl chloride (II) in 15 mL of tetrahydrofuran, in presence of 1 equivalent of diisopropylethylamine. The reaction mixture is stirred for 1 hour and then evaporated in vacuo. Following addition of ethyl acetate to the residue, there is obtained the hydrochloride of 3-(1-methyl-4-(1-methyl-4-formylaminopyrrole-2-aminocarbonyl)pyrrole-2-carboxamido)propionamidine (Ia, n=0).

EXAMPLE 5

3-(1-methyl-4-(1-methyl-4-aminopyrrole-2-aminocarbonyl)pyrrole-2-carboxamido)propionamidine (Ib, n=0)

The crude hydrochloride of 3-(1-methyl-4-(1-methyl-4-formylaminopyrrole-2-aminocarbonyl)pyrrole-2-carboxamido)propionamidine (Ia, n=0) from Example 4 is N-deformylated by treatment with 15 mL of a solution of hydrogen chloride in methanol for 1 hour (Step A). After evaporation of the solvent in vacuo, the residue is taken up with ethyl acetate to give the hydrochloride of 3-(1-methyl-4-(1-methyl-4-aminopyrrole-2-aminocarbonyl)pyrrole-2-carboxamido)propionamidine (Ib, n=0) (90% yield based on VII) whose analytical data are in agreement with the literature (F. Arcamone, et al., Gazz. Chim. Ital. 99:632 (1969).

EXAMPLE 6

Distamycin (Ia, n=1).

Following similar procedure as in Example 4, from the hydrochloride of 3-(1-methyl-4-(1-methyl-4-aminopyrrole-2-aminocarbonyl)pyrrole-2-carboxamido)-propionamidine (Ib, n=0) and crude 1-methyl-4-formylamino-2-pyrrolecarbonyl chloride (II) there is obtained Distamycin (Ia, n=1) after crystallization from water at pH 3.7 (70% yield) whose analytical data are in agreement with the above mentioned literature.

EXAMPLE 7

Higher Homologues (Ia and Ib, n≧2):

Distamycin hydrochloride is N-deformylated (Step A) as described in Example 5, and acylated (Step B) with crude 1-methyl-4-formylamino-2-pyrrolecarbonyl chloride (II) as described in Example 4 to give the compound (Ia, n=2). By repeating iteratively Step A and Step B, there are obtained all the higher homologues of general formula (Ia n≧2) and (b, n≧2), respectively.

EXAMPLE 8

Applicative Use

Distamycin (Ia, n=1) and Higher Homologues (Ia, n≧2).

This example illustrates the application of a disclosure of the present invention to modify and improve syntheses of the prior art [F. Arcamone, et al., Gazz. Chim. Ital. 97:1110 (1967); M Bialer, et al., Tetrahedron 34:2389 (1978); J. W. Lown, et al., J. Org. Chem. 50:3774 (1985); M Shibuya, et al., Heterocycles, 27:1945 (1988)] by reducing the number of hydrogenation steps of the nitro group and avoiding the N-formylation.

To 1-methyl-4-formylamino-2-pyrrolecarbonyl chloride (II) (16.0 mmol) dissolved in 80 mL of tetrahydrofuran are added diisopropylethylamine (18 mmol) and 3-aminopropionitrile (18 mmol) with continuous stirring for 1 hour. The reaction mixture is evaporated under vacuum and the resulting crude product is washed with water several times and dried to yield crude 3-(1-methyl-4-formylamino-2-carboxamido)propionitrile. This is N-deformylated by treatment with 30 mL of a solution of hydrogen chloride in methanol for 1 hour, the methanol is evaporated and the resulting crude product is crystallized from isopropanol/ethyl acetate to furnish 3-(1-methyl-4-amino-2-pyrrolecarboxamido)propionitrile hydrochloride, whose analytical data are in agreement with the above mentioned literature. This compound is acylated with 1-methyl-4-formylamino-2-pyrrolecarbonyl chloride (II) as above and subjected to the Pinner reaction to yield the hydrochloride of 3-(1-methyl-4-(1-methyl-4-aminopyrrole-2-aminocarbonyl)pyrrole-2-carboxamido)propionamidine (Ib, n=0)) from which Distamycin is obtained as described in Example 4.

Alternatively, 3-(1-methyl-4-amino-2-pyrrolecarboxamido)propionitrile is acylated with 1-methyl-4-formylamino-2-pyrrolecarbonyl chloride (II) and the resulting product is N-deformylated as above to yield 3-(1-methyl-4-(1-methyl-4-aminopyrrole-2-aminocarbonyl)pyrrole-2-carboxamido)propionitrile whose analytical data are in agreement with the above mentioned literature. This is acylated with 1-methyl-4-formylamino-2-pyrrolecarbonyl chloride (II) and the resulting product, after have been subjected to the Pinner reaction, is again acylated with 1-methyl-4-formylamino-2-pyrrolecarbonyl chloride (I) to give the 4-ring analogue of Distamycin.

EXAMPLE 9

Applicative Use

This example illustrates the application of a disclosure of the present invention to modify and simplify solid phase synthetic protocols of the prior art.

The appropriate resin is coupled to a variety of suitable linkers, for example as described in E. E. Baird & P. Dervan, J. Am. Chem. Soc., 118:6141 (1996); E. Vazquez et al., Tetr.

Lett., 40:3621 (1999); N. R Wurtz et al., Organic Lett., 3:1201 (2001). To the resin so obtained suspended and stirred in tetrahydrofuran is added the equivalent amount of crude 1-methyl-4-formylamino-2-pyrrolecarbonyl chloride (II) dissolved in small tetrahydrofuran, in the presence of 1 equivalent of diisopropylethylamine. The reaction mixture is stirred for 1 hour, the resin is then separated by filtration and washed with tetrahydrofuran.

Step (A): the washed resin is resuspended in a 1 N solution of hydrogen chloride in methanol and stirred for 1 hour to perform the N-deformylation of amino group. The resin is again separated by filtration, washed with water to neutral, then with methanol and tetrahydrofuran Step (13): the washed resin is resuspended in tetrahydrofuran and treated with the equivalent amount of crude 1-methyl-4-formylamino-2-pyrrolecarbonyl chloride (II) dissolved in small tetrahydrofuran, in the presence of 1 equivalent of diisopropylethylamine. The reaction mixture is stirred for 1 hour, the resin is then separated by filtration and washed with tetrahydrofuran.

Step (A) and Step (B) are repeated to obtain the polymer of the desired length. The final compounds are cleaved from the resin according to procedures described by the above mentioned authors.

The disclosures in Italian Patent Application No. MI2003A001111 from which this application claims priority are incorporated herein by reference.

What is claimed is:

1. Process for the manufacture of poly-(4-aminopyrrole-2-carboxamide) compounds of general formula (I):

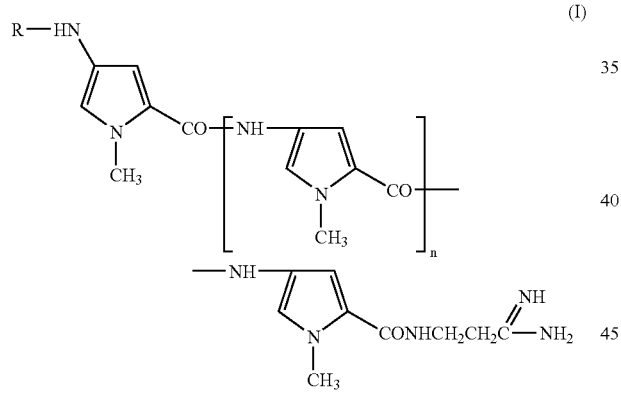
(I)

wherein: R is CHO or H; n is 0 or an integer comprised between 1 and 10 and, more specifically, (I) is (Ia) when R is CHO, and (I) is (Ib) when R is H, starting from and using the intermediate 1-methyl-4-formylamino-2-pyrrolecarbonyl chloride of formula (II):

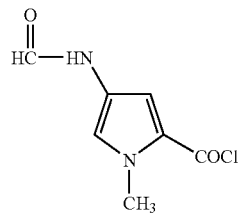
(II)

according to an iterative process entailing acylation and deformylation repeated steps, respectively.

2. The compound 1-methyl-4-formylaznino-2-pyrrolecarbonyl chloride of formula (II).

3. Process for obtaining the compound 1-methyl-4-formylamino-2-pyrrolecarbonyl chloride of formula (II) by reacting 1-methyl-4-fonnylanaino-2-pyrrolecarboxylic acid (V):

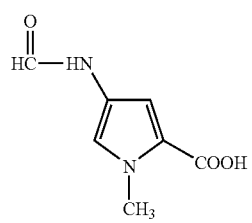
(V)

with a chlorinating agent.

4. Process according to claim 3, in which the chlorinating agent is thionyl chloride.

5. Process according to claim 1, in which the aminopyrroleamidine compound of formula (VII)

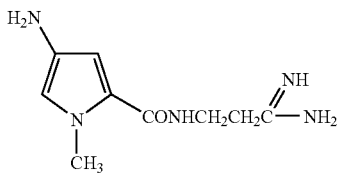
(VII)

is obtained from 1-methyl-4-formylamino-2-pyrrolecarbonyl chloride of formula (II) and 3-aminopropionitrile, and the resulting intermediate product is subjected to the Pinner reaction.

* * * * *